US007314755B2

(12) United States Patent  
Hand et al.

(10) Patent No.: US 7,314,755 B2  
(45) Date of Patent: Jan. 1, 2008

(54) PRESERVATION OF EUKARYOTIC CELLS USING REVERSIBLE PORE FORMATION

(75) Inventors: Steven C. Hand, Baton Rouge, LA (US); Michael A. Menze, Baton Rouge, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 371 days.

(21) Appl. No.: 10/965,039

(22) Filed: Oct. 14, 2004

(65) Prior Publication Data

US 2005/0084481 A1   Apr. 21, 2005

Related U.S. Application Data

(60) Provisional application No. 60/511,846, filed on Oct. 15, 2003.

(51) Int. Cl.
*C12N 5/00* (2006.01)
*A01N 1/02* (2006.01)

(52) U.S. Cl. ..................................... 435/374; 435/1.3
(58) Field of Classification Search ................ None
See application file for complete search history.

(56) References Cited

U.S. PATENT DOCUMENTS

| 6,045,990 | A | * | 4/2000 | Baust et al. ................. 435/1.1 |
| 6,127,177 | A | * | 10/2000 | Toner et al. ................ 435/374 |
| 2001/0019819 | A1 | | 9/2001 | Wolkers et al. ................ 435/2 |
| 2002/0009500 | A1 | | 1/2002 | Wolkers et al. ............. 424/532 |
| 2002/0076445 | A1 | | 6/2002 | Crowe et al. ................ 424/532 |
| 2002/0114791 | A1 | | 8/2002 | Crowe et al. ............ 424/93.21 |

OTHER PUBLICATIONS

American Heritage Dictionary, Fourth Edition, definition of "ambient", 2000.*
Wiley et al., "Genetic polymorphisms of human P2X7 receptor and relationship to function", Drug Development Research 53 (2-3): 72-76 (2001).*
Gibbons et al., "P2X7 receptors in rat parotid acinar cells: formation of large pores", Journal of Autonomic Pharmacology 21:181-190 (2001).*
McGill et al., "Temperature Cycling Preserves Platelet Shape and Enhances In-Vitro Test Scores During Storage at 4C", Journal of Laboratory and Clinical Medicine 92 (6) : 971-982 (1978).*
Arav et al., "Phase transition temperature and chilling sensitivity of bovine oocytes", Cryobiology 33 (6) : 589-599 (1996).*
Shen et al., "Superoxide radical-initiated apoptotic signalling pathway in selenite-treated HEPG2 cells: Mitochondria serve as the main target", Free Radical Biology and Medicine 30 (1) : 9-12 (2001).*
Buchanan, S. et al., "Abstract" (AAPS Biotechnology meeting, Boston, May 2004).

Buchanan, S. et al., "Permeabilization of hematopoietic progenitor cells to trehalose using P2Z purinoreceptor-associated pores for the purpose of cryopreservation," Exp. Hematology, vol. 32, issue 7, supp. 1, p. 79, abstract 196 (2004).
Chessell, I. et al, "Cloning and functional characterization of the mouse P2X7 receptor," FEBS Lett., vol. 439, pp. 26-30 (1998).
Crowe, L. et al., "Lessons from nature: the role of sugars in anhydrobiosis," Comp. Biochem. Physiol. A Mol. Integr. Physiol., vol. 131, pp. 505-513 (2002).
Crowe, J. et al., "The trehalose myth revisited: introduction to a symposium on stabilization of cells in the dry state," Cryobiology, vol. 43, pp. 89-105 (2001).
Elliott, G. et al., "Rapid loading of trehalose induced in J774 mouse macrophage cells," Cryobiology, vol. 47, p. 247 (2004).
Eroglu, A. et al., "Beneficial effect of microinjected trehalose on the cryosurvival of human oocytes," Fertil. Steril., vol. 77, pp. 152-158 (2002).
Eroglu, A. et al., "Intracellular trehalose improves the survival of cryopreserved mammalian cells," Nature Biotech., vol. 18, pp. 163-167 (2000).
Gan, B. et al., "Loading pyranine via purinergic receptors or hypotonic stress for measurement of cytosolic pH by imaging," Am. J. Physiolog., vol. 275, pp. C1158-C1166 (1998).
Guo, N. et al., "Trehalose expression confers desiccation tolerance on human cells," Nature Biotech., vol. 18, pp. 168-171 (2000).
Humphreys, B. et al., "Stress-activated protein kinase / JNK activation and apoptotic induction by the macrophage P2X7 nucleotide receptor," J. Biol. Chem., vol. 275, pp. 26792-26798 (2000).
Menze, M. et al., "Altering AMP:ATP ratio in mammalian cells to depress metabolic activity," Abstract and Poster presented at meeting of Society of Integrative and Comparative Biology (New Orleans, LA, Jan. 2004).

(Continued)

*Primary Examiner*—Sandra E. Saucier
(74) *Attorney, Agent, or Firm*—John H. Runnels; Bonnie J. Davis

(57) ABSTRACT

A method is disclosed for reliably stabilizing eukaryotic cells that express the $P2X_7$ receptor channel, particularly mammalian and other vertebrate cells, including human cells, for example mammalian macrophages, or hematopoietic stem cells, in order to introduce otherwise membrane-impermeable compounds that are helpful for stabilizing the cells during drying, chilling, freezing, freeze-drying, or cryopreservation. The cells are exposed to extracellular ATP in concentration sufficient to open pores in the plasma membrane. One or more otherwise membrane-impermeable compounds that aid the survivorship of cells are then introduced, for example, trehalose, and after a brief time the pores are closed—for example, by adding divalent cations, or by diluting the extracellular solution. Once the trehalose or other stabilizing compound has been introduced, the cells may be stably preserved. By taking advantage of an endogenous mammalian receptor and ATP, no antigenic compounds need be introduced.

27 Claims, 11 Drawing Sheets

OTHER PUBLICATIONS

Menze, M. et al., "Depression of cell metabolism and proliferation by membrane permeable and impermeable modulators: Role for AMP:ATP ratio," accepted for publication, Am. J. Phys. (in press, 2004), 288(2) : R501-R510 (2005).

Murgia, M. et al., "Characterization of the cytotoxic effect of extracellular ATP in J774 mouse macrophages," Biochem. J., vol. 288, pp. 897-901 (1992).

North, R., "Molecular physiology of P2X receptors," Physiol. Rev., vol. 82, pp. 1013-1067 (2002).

Puhlev, I. et al., "Desiccation tolerance in human cells," Cryobiology, vol. 42, pp. 207-217 (2001).

Steinberg, T. et al., "ATP permeabilization of the plasma membrane," Meth. Cell Biol., vol. 31, pp. 45-61 (1989).

Steinberg, T. et al., "ATP$^4$—permeabilizes the plasma membrane of mouse macrophages to fluorescent dyes," J. Biol. Chem., vol. 262, pp. 8884-8888 (1987).

Surprenant, A. et al., The cytolytic P2z receptor for extracellular ATP identified as a P2x receptor (P2X7), Science, vol. 272, pp. 735-737 (1996).

Virginio, C. et al., "Kinetics of cell lysis, dye uptake and permeability changes in cells expressing the rat P2X7 receptor," J. Physiol., vol. 519, pt. 2, pp. 335-346 (1999).

Wolkers, W. et al., "From anhydrobiosis to freeze-drying of eukaryotic cells," Comp. Biochem. Physiol. A. Mol. Integr. Physiol., vol. 131, pp. 535-543 (2002).

Wolkers, W. et al., "Human platelets loaded with trehalose survive freeze-drying," Cryobiology, vol. 42, pp. 79-87 (2001).

Sluyter, Ronald et al., "Extracellular ATP Increases Cation Fluxes in Human Erythrocytes by Activation of the P2X, Receptor," J. of Biological Chemistry, vol. 279, No. 43, pp. 44749-44755 (2004).

* cited by examiner

PRESERVATION OF EUKARYOTIC CELLS USING REVERSIBLE PORE FORMATION

The benefit of the Oct. 15, 2003 filing date of provisional application Ser. No. 60/511,846 is claimed under 35 U.S.C. § 119(e).

The development of this invention was partially funded by the Government under grant number N00173-01-1-G011 awarded by the Defense Advanced Research Projects Agency, and under grant number R01 GM071345-01 awarded by the National Institutes of Health. The Government has certain rights in this invention.

This invention pertains to an improved method for loading chemical agents into eukaryotic cells, such as vertebrate or mammalian cells, including human cells, and preserving those cells by drying, freezing, chilling, or freeze-drying.

There is an unfilled need for reliable methods to preserve eukaryotic cells by cryopreservation, chilling, or drying. There do exist some prior methods for preserving mammalian platelets by freeze-drying. There are considerably greater difficulties in the preservation of complex eukaryotic cells, including their nuclei and other organelles such as mitochondria, endoplasmic reticulum, Golgi apparatus, etc.

See, e.g., Wolkers et al., U.S. patent application 2001/0019819; Wolkers et al., U.S. patent application 2002/0009500; Crowe et al., U.S. patent application 2002/0076445; Crowe et al., U.S. patent application 2002/0114791; J. Crowe et al., "The trehalose myth revisited: introduction to a symposium on stabilization of cells in the dry state," *Cryobiology*, vol. 43, pp.89-105 (2001); L. Crowe et al., "Lessons from nature: the role of sugars in anhydrobiosis," *Comp. Biochem. Physiol. A Mol. Integr. Physiol.*, vol. 131, pp.505-513 (2002); W. Wolkers et al., "From anhydrobiosis to freeze-drying of eukaryotic cells," *Comp. Biochem. Physiol. A Mol. Integr. Physiol.*, vol. 131, pp.535-543 (2002); and W. Wolkers et al., "Human platelets loaded with trehalose survive freeze-drying," *Cryobiology*, vol. 42, pp. 79-87 (2001).

Numerous mammalian eukaryotic cells and cell lines are currently being used for many purposes, for example, the bioengineering of sheets of cells on synthetic matrices for use in repairing tissue damage such as burns, degenerative tissue damage, and bone or cartilage injury. There is an unfilled need for methods of storing such tissue layers and multicellular structures for long periods of time. Ultimately, preservation methods might even be used for entire organs.

One prior approach (an approach that has not been used clinically in humans) has been to use bacterial proteins to cause pore formation for loading of the disaccharide trehalose, which can stabilize the cell against drying when it is present on both sides of a lipid bilayer. However, the bacterial protein used can be antigenic.

Some animals are able to arrest their metabolism in response to severe environmental conditions such as hypoxia, desiccation, or freezing. These natural states of dormancy occur in phylogenetically diverse species such as the annual killifish *Austrofundulus limnaeus*; the tardigrade (or "water bear"), phylum Tardigrada; and the brine shrimp *Artemia franciscana*. The length of survival in a hypometabolic state is directly proportional to the degree of metabolic depression. There is evidence to support the hypothesis that activation of the AMP-activated protein kinase cascade could be part of the metabolic depression observed in some naturally occurring states of latency and the associated tolerance of severe environments. The 5'-AMP analogue Adenosine 5'-phosphorothioate (AMPS) mimics the action of AMP, but is resistance to modifications such as transphosphorylation in the presence of kinases, and exhibits a $K_m$ value approximately 6-fold lower than the natural effector 5'-AMP. However, the use of AMPS has previously been limited because its phosphorothioate group makes compound membrane-impermeable.

ATP (adenosine 5'-triphosphate) in sufficient concentration can induce the permeabilization of cell membranes via the $P2X_7$ receptor, and certain small molecules and ions may then pass through the resulting pores. It is recognized that there is a size limitation on molecules that can pass through the pores. However, to the inventors' knowledge, it has not previously been reported whether, or under what conditions, cells might survive $P2X_7$ receptor-based poration on a long-term basis. Some reports suggest that apoptosis may be the consequence of such poration. See, e.g., B. Humphreys et al., "Stress-activated protein kinase/JNK activation and apoptotic induction by the macrophage $P2X_7$ nucleotide receptor," *J. Biol. Chem.*, vol. 275, pp. 26792-26798 (2000); and C. Virginio et al., "Kinetics of cell lysis, dye uptake and permeability changes in cells expressing the rat $P2X_7$ receptor," *J. Physiol.*, vol. 519, pt. 2, pp. 335-346 (1999). P2receptors occur on the surface of many eukaryotic cell types, including, for example, mammalian erythrocytes.

T. Steinberg et al., "ATP permeabilization of the plasma membrane," *Meth. Cell Biol.*, vol. 31, pp. 45-61 (1989) reviews prior literature concerning the use of extracellular ATP to induce permeabilization of the plasma membrane towards certain molecules. The ATP-induced pore was reported to have a fairly well-defined size limitation. Small, water-soluble molecules and ions would pass through the plasma membrane following ATP-induced permeabilization—small molecules and ions such as phosphoinositide, calcium ion, p-nitrophenylphosphate, nucleotides, phosphate esters, lucifer yellow (443 Da), rubidium ion, sodium ion, potassium ion, carboxyfluorescein (376 Da), ethidium bromide (394 Da), and fura-2 (631 Da). However, trypan blue (961 Da) and Evans blue (869 Da) would not enter cells incubated with 20 mM ATP. Efflux of nucleotides and sugar phosphates from rat mast cells has been reported, but the cells would not admit insulin (~5000 Da) in the presence of ATP. The ATP-induced pores could be closed by removing ATP from the medium, or by adding divalent cations to the medium. Prolonged exposure of cells to ATP caused cell death. It was reported that more than 90% of J774 cells exposed to 10 mM ATP for 45 minutes would die. The usefulness of ATP permeabilization was said to be limited primarily by the range of cells that were responsive, and by the size of the induced membrane pore. Examples were given of uses for ATP permeabilization: as a research tool in studying the role of GTP-binding proteins in signal transduction, as a research tool in studying the role of calcium ions in signal transduction such as in macrophages, and as a research tool in studying organic ion transport in macrophages. Not all cell types were susceptible to ATP-induced permeabilization.

T. Steinberg et al., "$ATP^{4-}$ permeabilizes the plasma membrane of mouse macrophages to fluorescent dyes," *J. Biol. Chem.*, vol.262, pp.8884-8888 (1987) reported that extracellular ATP permeabilized the membranes of J774 cells to 6-carboxyfluorescein (376 Da), lucifer yellow (457 Da), and fura-2 (631 Da), but not to trypan blue (961 Da), Evans blue (869 Da) or larger dye conjugates.

B. Gan et al., "Loading pyranine via purinergic receptors or hypotonic stress for measurement of cytosolic pH by imaging," *Am. J. Physiolog.*, vol. 275, pp. C1158-C1166 (1998) reported the use of extracellular ATP to introduce the pH-sensitive dye 8-hydroxypyrene-1,3,6-trisulfonic acid (pyranine, 524 Da) into J774 or RAW cells to measure intracellular pH.

M. Murgia et al., "Characterization of the cytotoxic effect of extracellular ATP in J774 mouse macrophages," *Biochem. J.*, vol. 288, pp. 897-901 (1992) reported experimental data suggesting that, although extracellular ATP was known to be cytotoxic to many cell types, ATP did not cause apoptosis of J774 macrophages, and that it promoted a calcium- and sodium-independent colloido-osmotic lysis. The ATP-dependent cytotoxicity, but not the ATP-dependent increase in membrane permeability, was abrogated in sucrose medium.

The membrane ion channels that open in response to extracellular ATP are known as P2X receptors, of which there are several subtypes. See R. North, "Molecular physiology of P2X receptors," *Physiol. Rev.*, vol. 82, pp.1013-1067 (2002); A. Surprenant et al., "The cytolytic $P_{2z}$ receptor for extracellular ATP identified as a $P_{2x}$ receptor ($P2X_7$)," *Science*, vol. 272, pp. 735-737 (1996); I. Chessell et al, "Cloning and functional characterization of the mouse $P2X_7$ receptor," *FEBS Lett.*, vol. 439, pp. 26-30 (1998). A systematic study has not yet been undertaken as to which cells do, and which cells do not, express this receptor. Cells that do express the receptor include many cells of the immune system, including monocytes, macrophages, bone marrow cells, brain microglial cells, and hematopoietic stem cells.

To the knowledge of the inventors, there have been no prior suggestions for any practical uses for ATP permeabilization of cell membranes, other than various uses as a research tool.

Various methods have been explored to introduce non-native sugars such as trehalose into mammalian cells, such as pore formation with the toxin hemolysin, microinjection, and the expression of foreign genes to lead to trehalose expression. See A. Eroglu etal., "Intracellular trehalose improves the survival of cryopreserved mammalian cells," *Nature Biotech.*, vol. 18, pp. 163-167 (2000); A. Eroglu et al., "Beneficial effect of microinjected trehalose on the cryosurvival of human oocytes," *Fertil. Steril.*, vol. 77, pp. 152-158 (2002); N. Guo et al., "Trehalose expression confers desiccation tolerance on human cells," *Nature Biotech.*, vol. 18, pp. 168-171 (2000); and I. Puhlev et al., "Desiccation tolerance. in human cells," *Cryobiology*, vol. 42, pp. 207-217 (2001).

These procedures have inherent difficulties and limitations, such as the antigenicity of hemolysin, the difficulty of employing microinjection on a large scale, and the many difficulties inherent in the use of exogenous genes generally. To the knowledge of the inventors, there have been no prior suggestions for any practical means to cryopreserve or dessicate large numbers of vertebrate cells (other than gametes or platelets), at high efficiency, and then to restore the preserved cells, without the introduction of antigenic proteins, exogenous genes, or toxic preservatives such as dimethylsulfoxide.

We have discovered a method for reliably stabilizing eukaryotic cells, particularly vertebrate cells, and particularly cells that express the $P2X_7$ receptor channel—for example mammalian macrophages, and hematopoietic stem cells. Otherwise membrane-impermeable compounds are introduced into the cells to help stabilize the cells for preservation by drying, freezing, freeze-drying, chilling, or cryopreservation. The cells are exposed to free extracellular ATP in concentration sufficient to open pores in the plasma membrane. One or more otherwise membrane-impermeable compounds that aid the survivorship of cells are then introduced, for example, trehalose or metabolic modulators, and after a time the pores are closed—for example, by adding divalent cations, or by diluting the extracellular solution. Once the trehalose or other stabilizing compound has been introduced, the cells may be stably desiccated and later reconstituted. The pores are kept open for a time that is long enough to allow introduction of the stabilizing compound, but not so long that the cells become nonviable. It is preferred that the cells be allowed a recovery period between poration and preservation, as we have discovered that doing so enhances survival and reconstitution of the preserved cells. Surprisingly, the novel technique promotes long-term cell survival. The method may be used either with nucleated eukaryotic cells; or with non-nucleated eukaryotic cells, e.g., platelets and erythrocytes.

"Free extracellular ATP" refers to extracellularadenosine 5'-triphosphatethat is available for interaction with membrane receptors, i.e., ATP that is not bound to $Ca^{++}$ or $Mg^{++}$, and that is not otherwise chelated or bound in such a manner that it is unavailable for interaction with membrane receptors. Chelated ATP is far less effective than free ATP at opening these pores. At the appropriate time, the pores may be closed by reducing the concentration of free extracellularATP in a number of ways—by simple dilution; by binding to $Ca^{++}$, $Mg^{++}$, or another chelating agent; or by degrading it, e.g., with an ATPase.

In addition to trehalose, we have also successfully used the novel method to incorporate into cells the otherwise membrane-impermeable AMP, and the AMP analog AMPS (adenosine 5'-monophosphothioate). AMPS has the advantage that it functions at substantially lower intracellular concentrations than trehalose, meaning that the pores need not remain open as long to introduce an effective amount of the preservative. Compounds in addition to trehalose that should be useful in practicing the present invention include AMP, AMPS, sucrose, sorbitol, other sugars and combinations of sugars; other metabolic activators and inhibitors; and other impermeable protective or compatible osmolytes such as di- or oligosaccharides, sarcosine, octopine, taurine, proline, betaine, pinitol, ectoine, N-acetyl lysine, glycosylglycerate, and sulfotrehalose. Trehalose is preferred because it is a non-reducing sugar, meaning that it does not readily react with the amine groups of proteins, which can be harmful; the conformation of trehalose promotes interdigitation between phospholipid head groups; and it has a large hydration radius. Cells that have been preserved by this method may be reconstituted by incubation in cell culture medium, preferably in medium that has been pre-warmed to 37° C.

By taking advantage of an endogenous mammalian receptor and ATP, no antigenic compounds need be used. Thus the introduction of preserved and reconstituted cells into a recipient need not induce an immunological response that is substantially different from the immunological response (if any) that would be induced by the administration of otherwise identical cells that had not been preserved and reconstituted in accordance with the present invention.

Leaving the pores open too long (typically, for more than about 45 minutes if the cells are held at 37° C.) can cause excessive mortality. Rather, one opens the pores with ATP, loads the cells with trehalose, closes the pores, allows the cells to recover, and then desiccates the cells. Preferably, the pores are allowed to remain open for only about 15-30 minutes at 37° C. Optionally, to increase the amount of material loaded into the cells while avoiding excessive cell mortality, the pores may first be opened at a temperature between about 30° C. and about 40° C., preferably about 37° C.; and after about 1 to about 20 minutes, preferably about 10 minutes, the cells are cooled to about 0° C. to about 10° C., preferably about 4° C.; and the pores are then left open at this cooler temperature for about 30 minutes to about 2 hours, preferably about 1.5 hour. The cells are then returned to 37° C., and the pores are closed, preferably by diluting the concentration of free ATP by adding new culture medium.

In early (unpublished) work by our group, in which we attempted to reproduce the results reported in the literature cited above concerning ATP-induced cell poration, we found that the porated cells invariably died, usually within about 24 hours. We observed that various dyes were indeed taken up by the cells as reported in the literature. But, at least in our experiments, we also invariably observed that the cells died soon thereafter.

We subsequently discovered how to prevent this mortality. In particular, we discovered the importance of causing the pores to close after a relatively short time, the importance of which has not previously been suggested. Earlier papers on ATP-induced pores reported studies on the opening and closing of pores, but said nothing concerning long-term survival. We therefore speculate that, although the work reported in the earlier references may have resulted in the uptake of certain molecules as described there, the cells thereafter became nonviable. In other words, although cellular metabolism may have continued for a short time after extracellular ATP treatment—on the order of a few hours to a day—at longer periods of time the cells likely died, even though that outcome was not reported in the literature. In any event, the earlier references known to the present inventors do not suggest any method for enhancing long-term survival of the treated cells.

We have also discovered that survivorship and reconstitution of preserved cells was enhanced by allowing the cells a recovery time (preferably on the order of about eighteen hours) between poration and dehydration or freezing. Optionally, an apoptosis inhibitor such as cyclosporin A may be added to the cells during the recovery period. Cyclosporin A, for example, can cross cell membranes without the necessity of opened pores.

Our preferred poration medium comprises 50 mM $K_2HPO_4/KH_2PO_4$ buffer (pH 7.0), 250 mM trehalose, 1 mM $MgSO_4$, and 5 mM glucose, supplemented with 1× basal Eagle's medium vitamin solution (Gibco 21040-050) and 1× MEM amino acids solution (Invitrogen, Grand Islands, N.Y.). Total osmotic pressure of the poration buffer is about 365 mOsm. To open the pores, ATP is added to a final concentration between about 0.5 and 20 mM, preferably about 5 mM. In future experiments we will examine the effect of varying the concentrations of these components, e.g., varying pH between about 7 and about 8, and varying the trehalose concentration between about 10 and about 1000 mM.

If the solution is too acidic, too much ATP may bind to protons, thereby rendering free ATP unavailable to stimulate pore opening. For example, we have discovered that under standard incubation conditions for mammalian cells, the $CO_2$ concentration (typically ~5-10%) makes the solution too acidic for efficient formation of ATP-induced pores. Contrary to the usual procedures used for mammalian cell culture, we found that it is advantageous to remove $CO_2$ from the environment of the cells during poration, in order to promote a higher pH and thereby to make more ATP available for pore formation. The pH is preferably from about 6.5 to about 8, preferably about 7.0. The desired pH may be achieved, for example, by adjusting a buffered solution, for example by adjusting phosphate-buffered saline (PBS) with a base such as NaOH or KOH; or if necessary, by back-titrating with an acid such as HCl or $H_3PO_4$.

The genes encoding the mouse, rat, and human $P2X_7$ receptors have been cloned, inserted into plasmids, and sequenced. Plasmids containing the cloned $P2X_7$ receptor gene may be used in accordance with techniques known in the art to transfect other cells or cell lines as needed, whether for experimental purposes or to induce expression of the gene in cells where expression of the receptor is low or absent. By placing the gene under the control of a constitutive promoter known in the art (e.g., SV40), high expression may be obtained. By using an expression vector known in the art that does not incorporate into the genome, transient expression of the $P2X_7$ receptor may be obtained without permanently altering the genetic makeup of the cells, a feature that may be particularly attractive when this technique is used therapeutically in humans. Transfection and expression (or overexpression) of the $P2X_7$ receptor is straightforward using standard techniques known in the art for transfection and expression of exogenous genes in mammalian and other eukaryotic cells. See, e.g., I. Chessell et al, "Cloning and functional characterization of the mouse $P2X_7$ receptor," *FEBS Lett.*, vol. 439, pp. 26-30 (1998); and GenBank accession numbers Y09561 (human), X95882 (rat), and AJ009823 (mouse).

MATERIALS AND PROCEDURES

Cells

Figure 1:
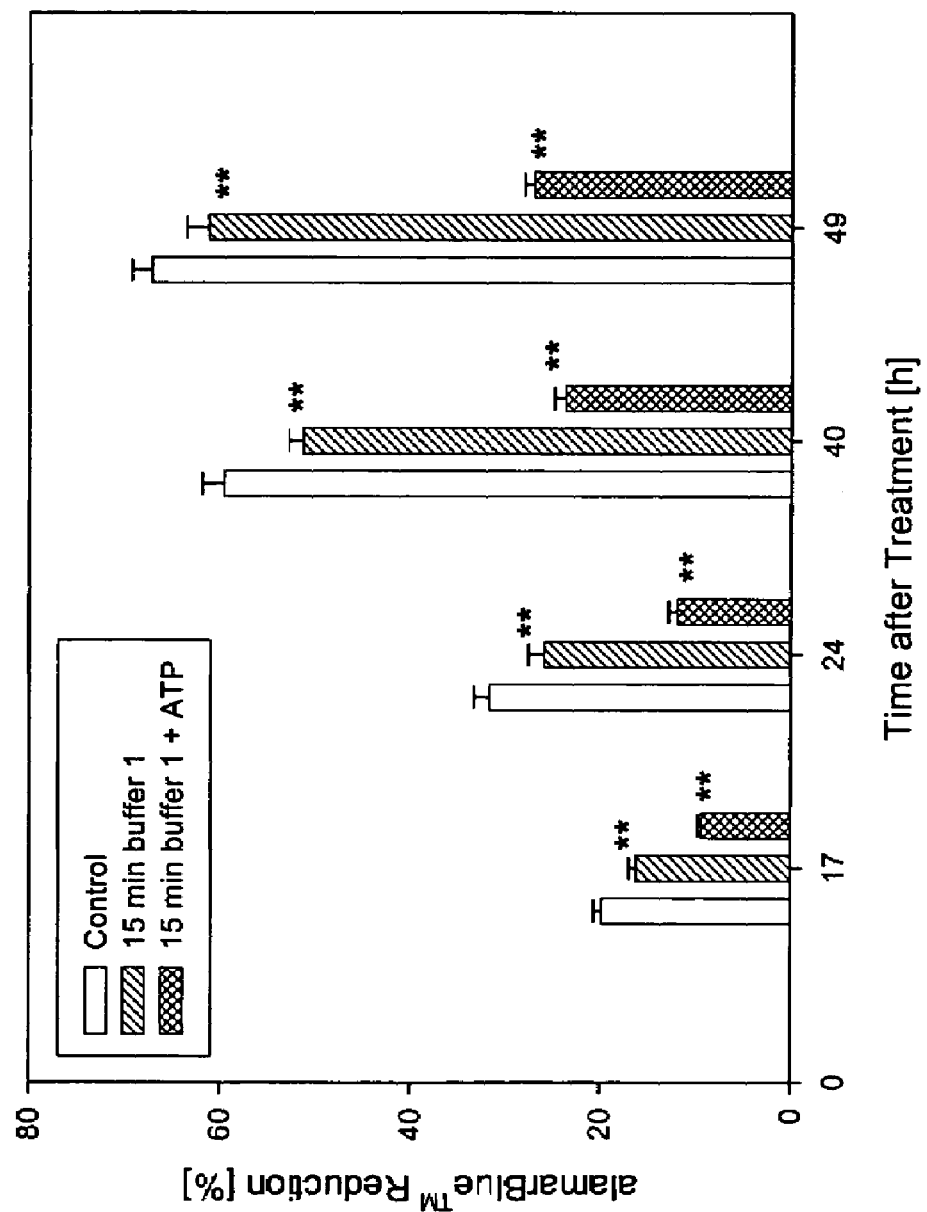
FIG. 1 depicts the effect of ATP-dependent poration on the metabolism of J774 cells as a function of time after treatment.

J774.A1 mouse macrophage cells (ATCC, Manassas, Va.) were grown in 75 cm² cell culture flasks (Corning Incorporated, Corning, N.Y.) containing a standard culture medium of Dubelco's modified Eagle's medium without sodium pyruvate, supplemented with 10% fetal bovine serum, 100 units/mL penicillin, 100 μg/mL streptomycin, and 2 mM glutamine ("DMEM") (all from Invitrogen, Grand Islands, N.Y.). The cells were maintained in a humidified atmosphere of 10% $CO_2$ and 90% air at 37° C. The number of cells per flask was determined with a hemocytometer after removal with a cell scraper. To obtain a large number of cells for the experiments, about $5\times10^6$ cells were transferred to a spinner flask containing 100 mL of standard culture medium. The spinner flask cultures were allowed to grow to a maximum cell density of about $4$–$8\times10^5$ cells/mL by frequent exchange of medium. All cells were cultured in suspension for at least 3-5 days prior to use in experiments.

ATP-dependent Cell Poration via the $P2X_7$ Receptor Channel

To introduce compounds that were otherwise membrane-impermeable into the cytoplasm, J774.A1 cells were centrifuged at 175 g; and were then resuspended in Buffer 1 (50 mM $K_2HPO_4/KH_2PO_4$, pH 7.0, 365 mOsm, 250 mM trehalose, 1 mM $MgSO_4$, 5 mM glucose, supplemented with Basal Medium Eagle Vitamin Solution and MEM Amino Acids Solution (Invitrogen, Grand Islands, N.Y.), with each of the last two components diluted to 1×). An ATP stock solution (50 mM) was prepared in phosphate buffered saline (Invitrogen, Grand Islands, N.Y.) adjusted to pH 7.4 with 6M KOH, and stored at −80° C. In some experiments, $5\times10^6$ to $6\times10^7$ cells were resuspended in 900 µL of buffer 1 to which 100 µL of ATP stock solution had been added. The cells were incubated for 15 min or 30 min at 37° C. in sealed microtubes.

To close the $P2X_7$ receptor channels, the cell suspensions were diluted about 100 fold with standard culture medium that had previously been equilibrated in 10% $CO_2$ and 90% air.

Cell Viability Assays

To assess the effect of ATP-induced permeability on cell viability, cells were grown in suspension after activation and subsequent closure of the $P2X_7$ receptor, as described above. Aliquots of cell suspension were removed from the spinner flask at various intervals. The number of viable cells at different times was determined by counting with a hemocytometer after diluting the sample 1:1 with a 0.4% Trypan blue solution (Sigma, St. Louise, Mo.). Alternatively, cell viability was assessed by monitoring the metabolic activity of the cells with AlamarBlue™ (BioSource International, Inc., Camarillo, Calif.). AlamarBlue™ stock solution was added to a final concentration of 10% (v/v) in standard culture medium without phenol red. Then 2 mL of the 10% AlamarBlue™ solution was added to each well of a 12 well Nunclun™ multidish (Fischer Scientific, Pittsburgh, Pa.). After adding 20,000 to 40,000 cells to each well, absorbances at $\lambda=570$ nm and $\lambda=600$ nm were measured with a micro plate reader (Spectra$_{max}$ Plus, Molecular Devices, Sunnyvale, Calif.) at different times. The amount of reduced AlamarBlue™ was calculated as: RA %=$[A_{570}-A_{600}\times R_o]\times$ 100%, where $A_{570}$ and $A_{600}$ are the absorbances at $\lambda=570$ nm and $\lambda=600$ nm, respectively, after subtracting the base level of absorbance of standard culture medium without AlamarBlue™, and where $R_o$ is the ratio $A_{570}/A_{600}$ for the standard medium containing 10% AlamarBlue™.

High Performance Liquid Chromatography of Nucleotides

Acid soluble extracts of cell suspensions were prepared by adding ice-cold 70% perchloric acid to a final concentration of 7% (w/v). Acid insoluble fractions were removed by centrifugation for 10 min at 10,000 g and 4° C. (Eppendorf Centrifuge 5417R, Fischer Scientific, Pittsburgh, Pa.). Extracts were neutralized with ice-cold 5 M $K_2CO_3$, and were stored at −80° C. until analyzed. The potassium perchlorate precipitate was removed by centrifugation as above. Analyses were performed using a Dionex HPLC system, including a GP 50 gradient pump, an AS 50 auto-sampler and an AS 50 thermal compartment (Dionex, Sunnyvale, Calif.). Aliquots of the supernatant were applied to a 4.6 mm×25 cm reverse-phase column (Synergy 4M Hydro RP 80A, Phenomenex, Torrance, Calif.),and eluted isocratically for 15 min with a starting buffer of 50 mM $K_2HPO_4/KH_2PO_4$, pH 6.2, containing 10 mM tetrabutyl-ammonium hydrogen sulfate (Sigma, St. Louise, Mo.) at a flow rate of 1 mL/min at 30° C. Then a linear gradient from 0% to 25% acetonitrile was applied over 40 min. Absorbance of the effluent was monitored with a PDA-100 photodiode array detector (Dionex, Sunnyvale, Calif.) at wavelengths from $\lambda=190$ nm to $\lambda=390$ nm. Peaks were identified by comparison with retention times of standards, as well as by analyzing peak spectra between $\lambda=190$ nm and $\lambda=390$ nm from a recorded 3D-field with Chromeleon™ software (Dionex, Sunnyvale, Calif.). Concentrations of nucleotides were determined from a measurement of peak area at $\lambda=260$ nm. Calibration curves were linear over the range assayed.

Calorimetric Measurements

Calorimetric measurements were conducted to assess the influence of various treatments on the total energy flow of J774 cells. A 2277 thermal activity monitor (LKB Produkter, Bromma, Sweden) was used to measure the heat dissipation of J774 cells in suspension. A 4 mL static ampule charged with 2.7 mL water was used as a reference vessel. Static and dynamic calibrations against water in both ampules were performed before the experimental heat signals were measured. For the experiments, the sample ampule was charged with 2.7 mL of cell suspension. An aliquot of the spinner flask culture was diluted with standard culture medium to give 130,000-250,000 cells in 2.7 mL, which was equilibrated with 10% $CO_2$ and 90% air. All calorimetric measurements were performed at 37° C. A two-hour period was allowed for thermal equilibration after lowering the ampule into the calorimeter. The power signal was then recorded for the next 20 hours. The ongoing proliferation of the cells produced a continuous increase in the heat signal during the measurements. Heat dissipation of J774 cells was measured 3 and 24 h after poration in buffer 1 containing 5 mM ATP.

Results

EXAMPLE 1

In one series of experiments, we assessed the metabolic influence of ATP-dependent poration as a function of time following treatment. Suspended J774 cells (40,000 per well) were incubated for 15 minutes in Buffer 1 without added ATP, or in Buffer 1+5 mM ATP (experimental), or were left untreated (control—just plated in the same concentration as the treated cells). The effect of the treatments on cell metabolism was assayed via AlamarBlue™ reduction. As shown in FIG. 1, metabolic activity in Buffer 1 was reduced by about 13%, while metabolic activity in Buffer 1+ ATP (porated cells) was reduced by about 50%. Each bar in FIG. 1 represents the mean±standard deviation for three different experiments. A pair of asterisks for a bar at a given time indicates a statistically significant difference from control ($P<0.05$). (Controls increased with time, presumably as the result of normal cell growth.)

EXAMPLE 2

Figure 2:
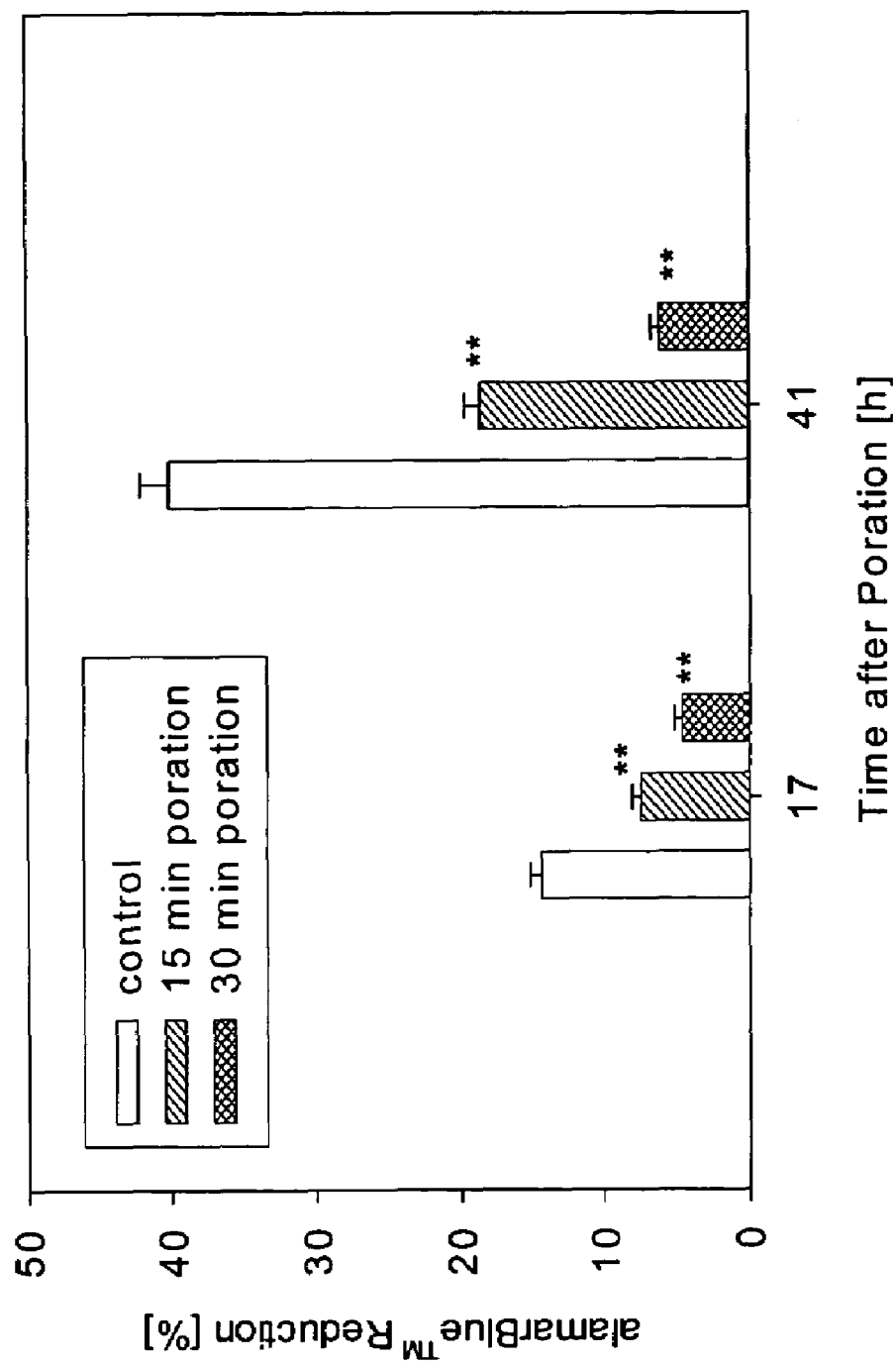
FIG. 2 depicts the effect of ATP-induced pore opening time on the metabolism of J774 cells at seventeen and forty-one hours after treatment.

In this series of experiments, we assessed the effect of the duration of pore opening time on the metabolic activity of J774 cells. Suspended J774 cells (35,000 per well) were incubated for 15 or 30 minutes in Buffer 1+5 mM ATP. The effect of the treatments on cell metabolism was assayed via AlamarBlue™ reduction. As shown in FIG. 2, metabolic activity decreased substantially when poration time increased from 15 minutes to 30 minutes, as measured at 17 hours and 41 hours after treatment. Each bar in FIG. 2 represents the mean±standard deviation for three different experiments. A pair of asterisks for a bar at a given time indicates a statistically significant difference from control ($P<0.05$). (Again, controls increased presumably as the result of normal cell growth.)

EXAMPLE 3

Figure 3:
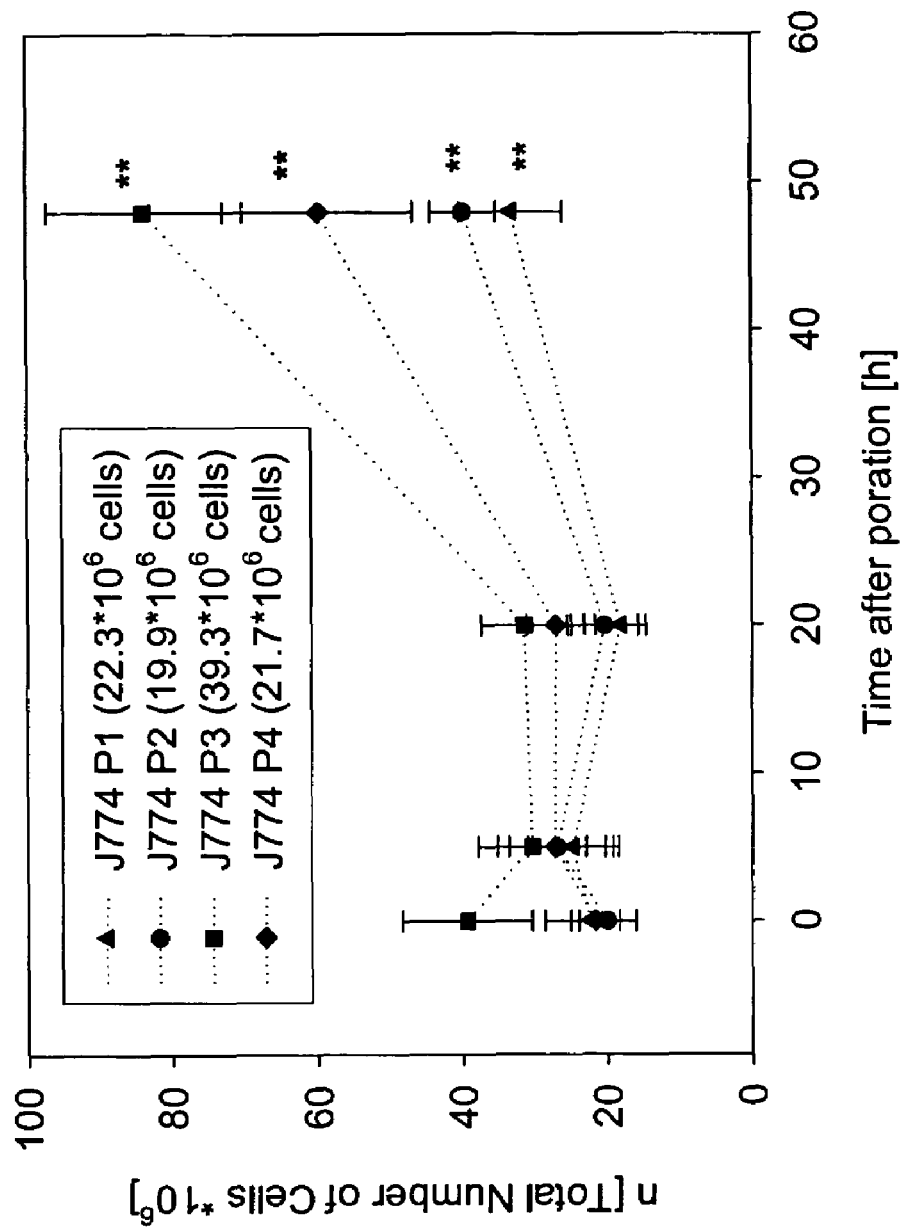
FIG. 3 depicts the proliferation of J774 cells as a function of time following treatment.

In another series of experiments, we assessed the degree to which cell proliferation was suspended following poration. Suspended J774 cells were incubated for 15 minutes in Buffer 1+5 mM ATP. Cell counts for each of four different replicates (P1, P2, P3, and P4) are shown in the legend in FIG. 3. Following a 15-minute poration, the cells were transferred to a spinner flask containing 100 mL of 10% $CO_2$-equilibrated cell culture medium. Cell counts were taken at several different times, as shown in FIG. 3. After poration, cell proliferation stopped for approximately 20 hours, and then resumed at a typical rate. Each point in FIG. 3 represents the mean±standard deviation for ten cell counts. A pair of asterisks at 48 hours indicates a statistically significant increase ($P<0.05$) in cell number as compared to that seen at 20 hours.

EXAMPLE 4

Figure 4:
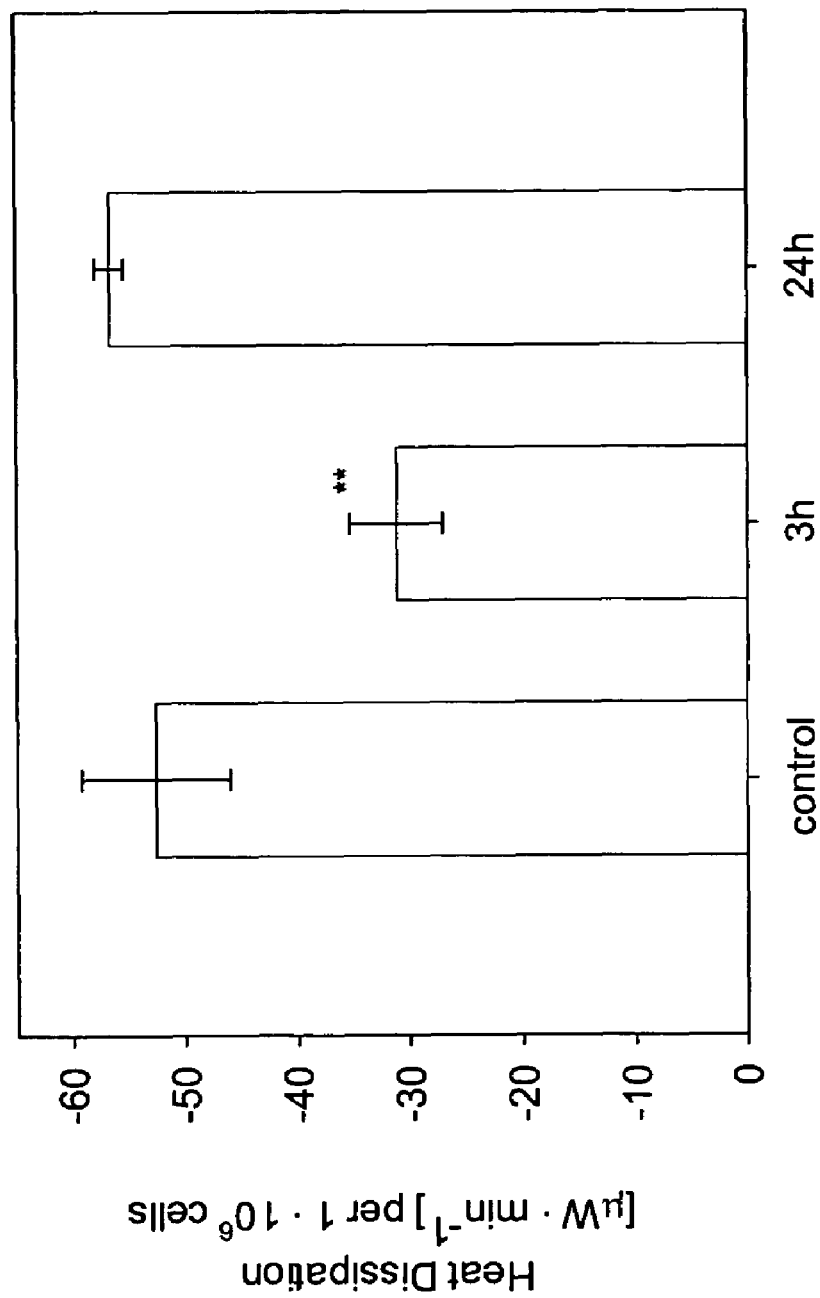
FIG. 4 depicts the influence of ATP-poration on heat dissipation of J774 cells.

In this series of experiments, we assessed the influence of ATP-induced poration on the heat dissipation of J774 cells. Heat dissipation was measured 3 hours and 24 hours after poration in buffer 1+5 mM ATP. As shown in FIG. 4, heat dissipation 3 hours after poration was significantly reduced as compared to control cells. By 24 hours after poration, the heat signal was indistinguishable from that for the untreated control cells. Each bar in FIG. 4 represents the mean±standard deviation for three to six separate measurements. The pair of asterisks for the bar at three hours indicates a statistically significant difference from control ($P<0.05$).

EXAMPLE 5

Figure 5A:
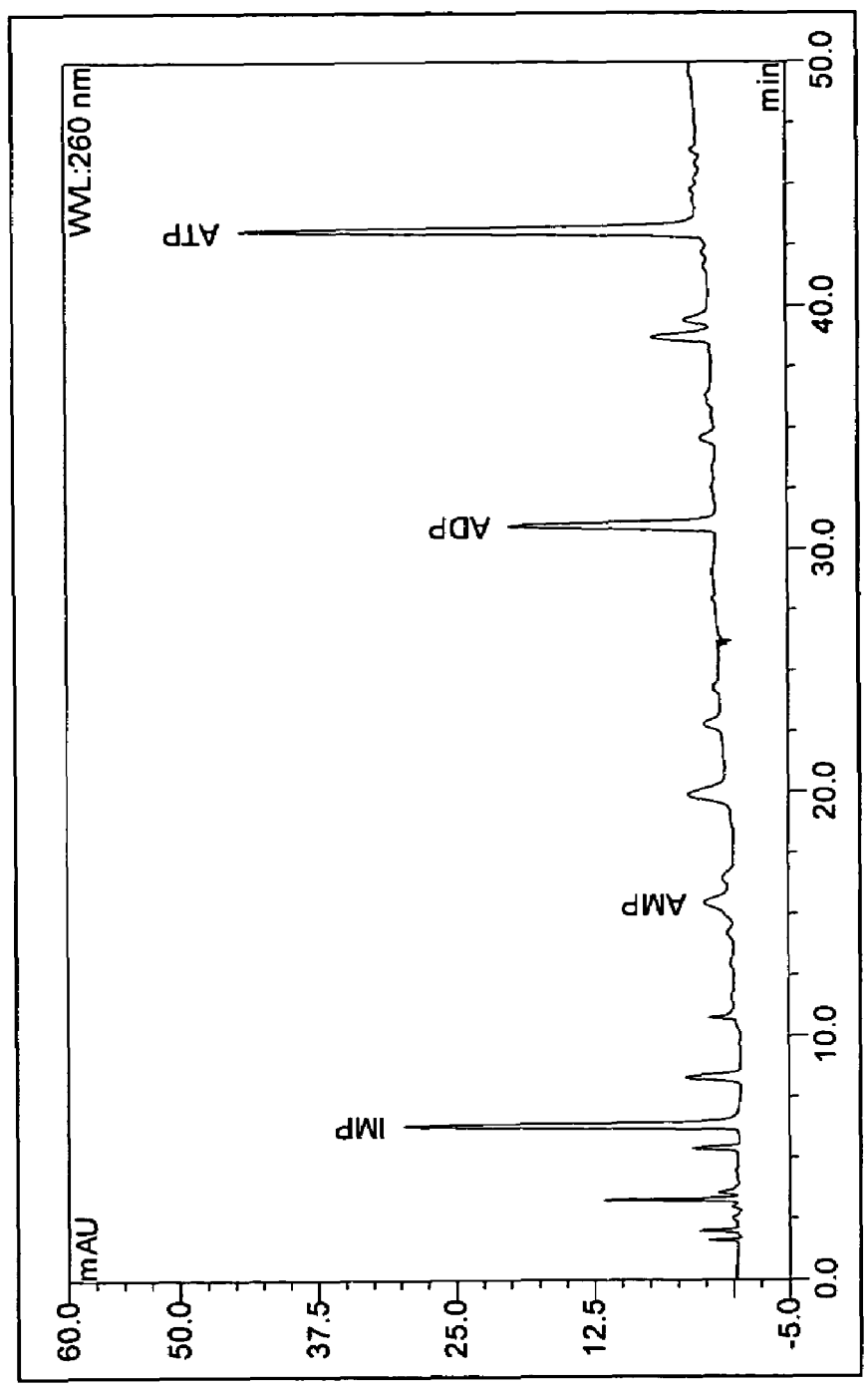
FIGS. 5A and 5B depict HPLC chromatograms of the loading of J774 cells with AMP and the analog AMPS, respectively, following ATP-induced poration.
Figure 5B:
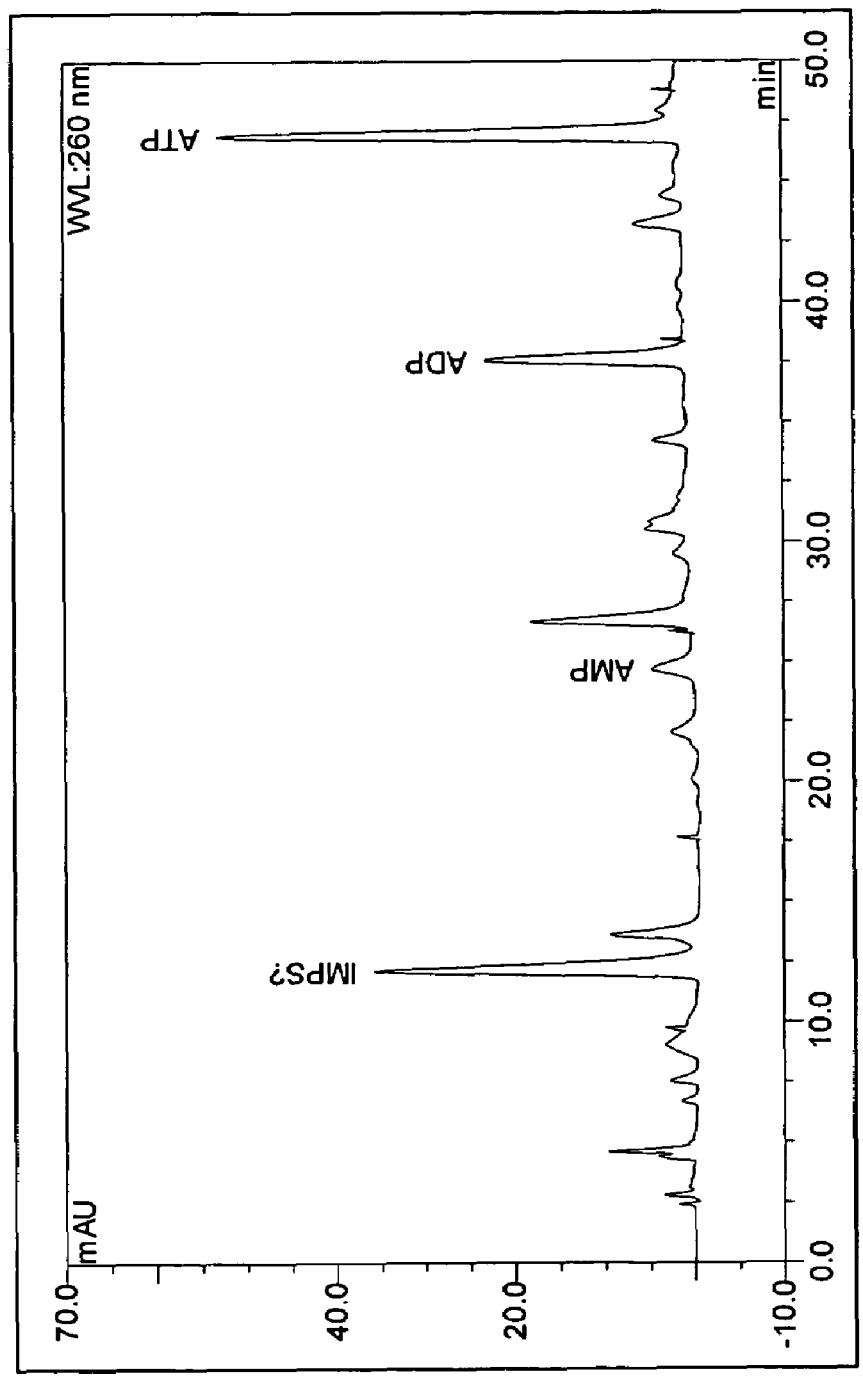

In this series of experiments, we observed the uptake of AMP and the AMP analog AMPS in cells porated by extracellular ATP. J774 cells were porated for 20 minutes at 37° C. in DMEM (pH 7.4) by adding 5 mM ATP. During poration, the cells were exposed to 5 mM AMP, or to 3.5 mM AMPS. Cells were extracted with perchloric acid after incubation. FIG. 5(A) depicts an HPLC chromatogram of the extracted AMP-loaded cells, and FIG. 5(B) depicts an HPLC chromatogram of the extracted AMPS-loaded cells. From the chromatograms, we concluded that loading the cells with AMP led to an increase in ADP, and a substantial increase in IMP (inosine monophosphate). Loading the cells with AMPS led to substantial production of a new compound, perhaps the deaminated form of AMPS (inosine 5'-monophosphothioate, or IMPS).

EXAMPLE 6

Figure 6:
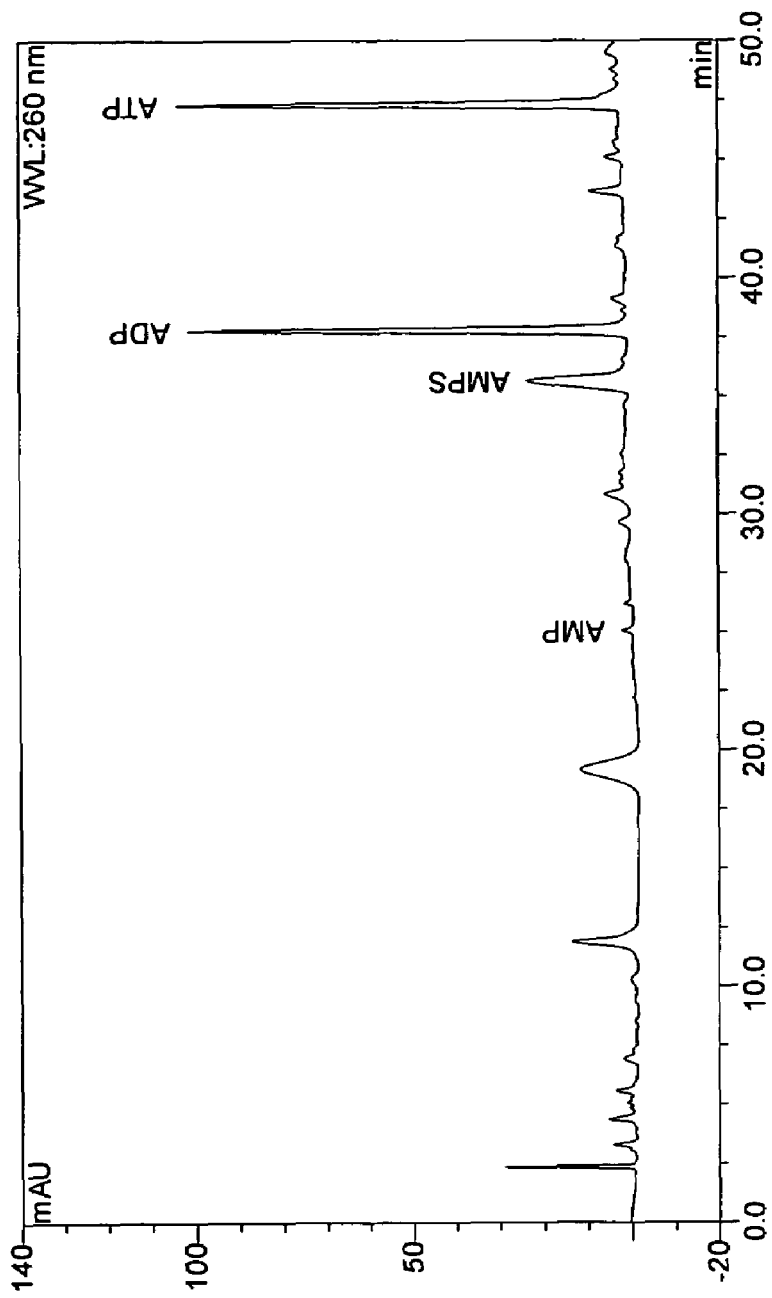
FIG. 6 depicts an HPLC chromatogram of the loading of J774 cells with AMPS under conditions where AMP-deaminase was inhibited.

In this experiment, we observed more directly the uptake of AMPS in cells porated by extracellular ATP. The experiment was otherwise conducted as described in Example 5 and illustrated in FIG. 5(B), except that cellular AMP-deaminase was inhibited by adding 35 µM coformycin to the medium. Results are shown in FIG. 6. The HPLC chromatogram shows that inhibition of AMP-deaminase inhibited the metabolism of AMPS in the cells, and consequently a substantial intracellular concentration of AMPS was observed, particular as compared to that seen in FIG. 5(B).

EXAMPLE 7

Figure 7:
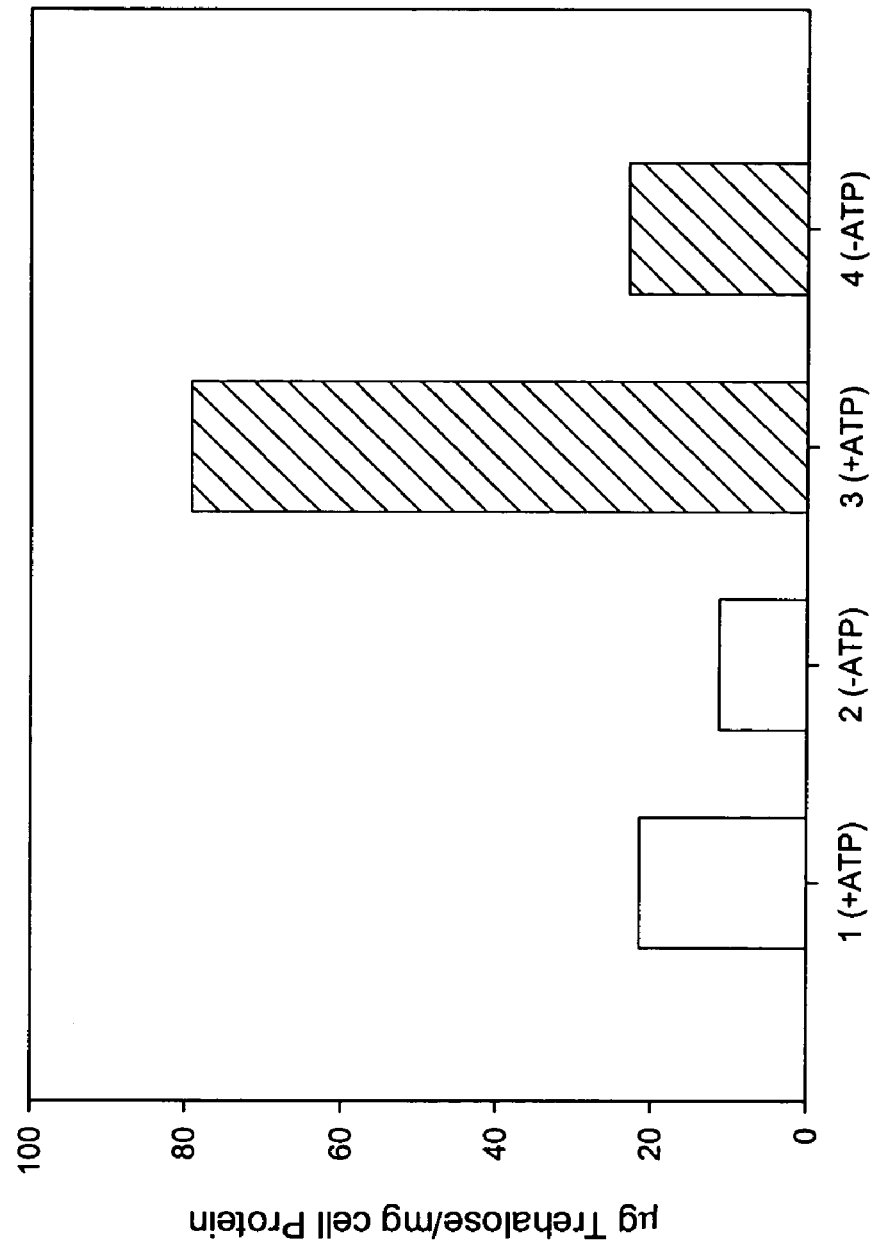
FIG. 7 depicts the loading of trehalose into J774 cells as a function of incubation times for controls and for cells treated with ATP.

In this series of experiments, we observed the uptake of trehalose in cells porated by extracellular ATP. J774 cells were incubated for different times in Buffer 1 (=ATP−), or in Buffer 1+5 mM ATP (=ATP+). Cell extracts were assayed for trehalose concentrations by separating carbohydrate peaks on a Hamilton RCX10 column, and then analyzing using pulsed amperometric electrochemical detection with an ESA Coulochem cell. FIG. 7 depicts uptake of trehalose with and without ATP. The white bars are results from treatment for 15 minutes at 37° C. The cross-hatched bars are results from treatment for 15 minutes at 37° C., followed by 2 hours at 0° C. Some uptake of trehalose was observed in the absence of extracellular ATP, presumably due to pinocytosis or to depolarization of the plasma membrane. The ATP-treated cells showed a significantly higher trehalose uptake, and the differential between ATP-treated and control cells increased with increasing incubation time. Each bar in FIG. 7 represents the mean of several different measurements. Although leaving the pores open for the longer periods of time at 37° C. can lead to cell death, the pores may be left open for longer periods at lower temperatures, while still leaving the cells viable and still allowing higher uptake of trehalose. At least 40% of the cells survived this treatment. We expect that the survivorship percentage will be improved by reducing the time the cells are held at 37° C. prior to chilling; future experiments will be done along these lines. Also, we have found that in the absence of pore opening, some compounds, such as AMPS, are taken up by the cells in only negligible concentrations in the absence of ATP (data not shown).

We have obtained superior results by opening the pores at physiological temperatures, then chilling the cells, allowing the pores to remain open for an extended time at the lower temperature, and then closing the pores. Without wishing to be bound by this theory, it is believed that these superior results may be explained by the following mechanism: Metabolism is slowed substantially by chilling the cells. Thus many of the adverse effects of leaving cell pores open may be delayed by chilling. However, so long as the medium remains liquid and its viscosity does not increase substantially, the rate of diffusion is not strongly affected by the reduction in temperature. (To a first approximation, the rate of diffusion is proportional to the absolute temperature. Thus, all else being equal, the rate of diffusion at 0° C.=273° K. is not dramatically slower than the rate of diffusion at 37° C.=310° K.) Thus chilling allows diffusion of the preservative (e.g., trehalose) through the open pores to continue at nearly the same rate, while mitigating at least somewhat the adverse effects to the cells of allowing the pores to remain open for an extended time.

EXAMPLE 8

Figure 8:
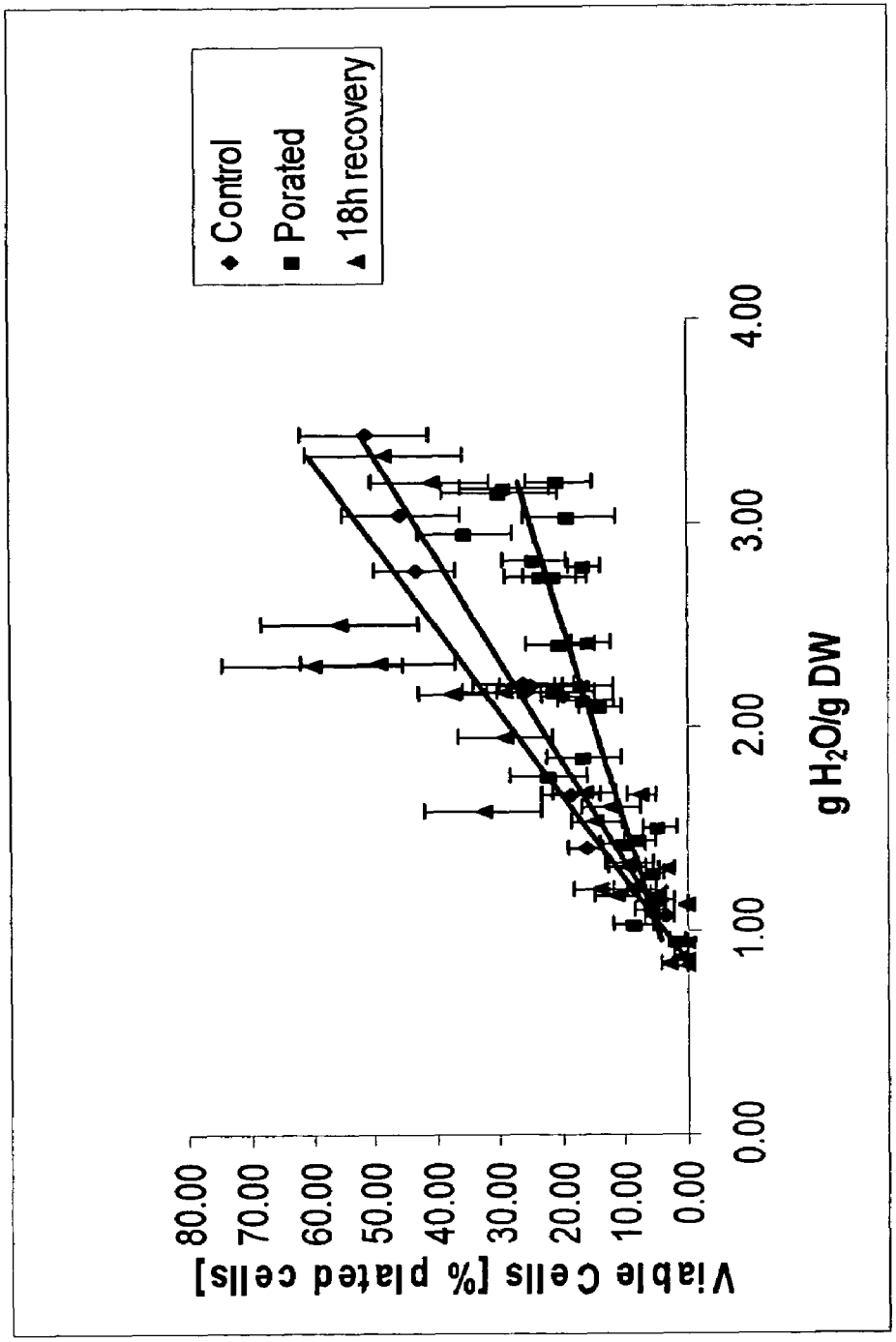
FIG. 8 depicts the recovery of J774 cells as a function of moisture content for various treatments.

In this series of experiments, we assessed the effect of allowing cells a period of recovery after poration, prior to drying. Control J774 cells received no poration treatment prior to drying. Experimental poration-only J774 cells were porated for 5 minutes at 37° C. as otherwise described above, and were then held 60 minutes at 0° C. prior to drying. Experimental poration-plus-recovery cells in Buffer 1 (with trehalose) were treated as were the poration-only cells in Buffer 1 (with trehalose), except that they were given an 18-hour recovery period in DMEM cell culture medium after poration and prior to drying. After-these treatments, the cells were air-dried in diluted DMEM containing 200 mM trehalose, to different moisture levels (g $H_2O$/g dry weight), as shown in FIG. 8. We pipetted 10 droplets of cells (each 15 µL) onto cell culture dishes. Cells were dried at ambient temperature (20-25° C.) in a desiccator cabinet containing Drierite™ desiccant (W.A. Drierite Co., Xenia, Ohio). Water loss from cell samples was measured gravimetrically as a function of time. Water content is expressed as grams water per gram dry mass. (Sample dry mass was determined by drying cell culture dishes containing 10 droplets of cell samples for 12 hours at 60° C.) After reaching the indicated moisture levels, cells were re-hydrated by adding DMEM cell culture medium to the culture dishes. Cells were then placed in a cell culture incubator at 37° C. under a humidified atmosphere containing ~10% $CO_2$ and ~90% air. Cell counts were performed the next day, and the number of cells having intact membranes (viable cells) was measured by trypan blue exclusion. FIG. 8 depicts the percentage of plated cells thus determined to have intact membranes, for the different moisture levels and pre-drying treatments. Each point in FIG. 8 represents mean±standard deviation for 10 cell counts. As shown in FIG. 8, porated cells without recovery had lower viability than did the control cells, but the porated cells allowed 18 hours recovery displayed higher viability. Also, higher moisture levels improved viability for all three regimes. The slopes of all three lines in FIG. 8 were statistically different from one another ($P<0.005$) as determined by a slope analysis conducted according to the method of Zar, *Biostatistical Analysis* (1999). ATP-poration in trehalose, followed by an 18-hour recovery phase, significantly improved dessication tolerance as compared both to control and to ATP-porated cells not allowed a period of recovery.

EXAMPLE 9

The novel technique will also be used to enhance the survival of cells stored by chilling. The technique as otherwise described above will be used to introduce trehalose (or another preservative) into cells, which will subsequently be stored by chilling (e.g., to 4° C.) without freezing. It is expected that survival of the cells will be enhanced.

EXAMPLE 10

Figure 9:
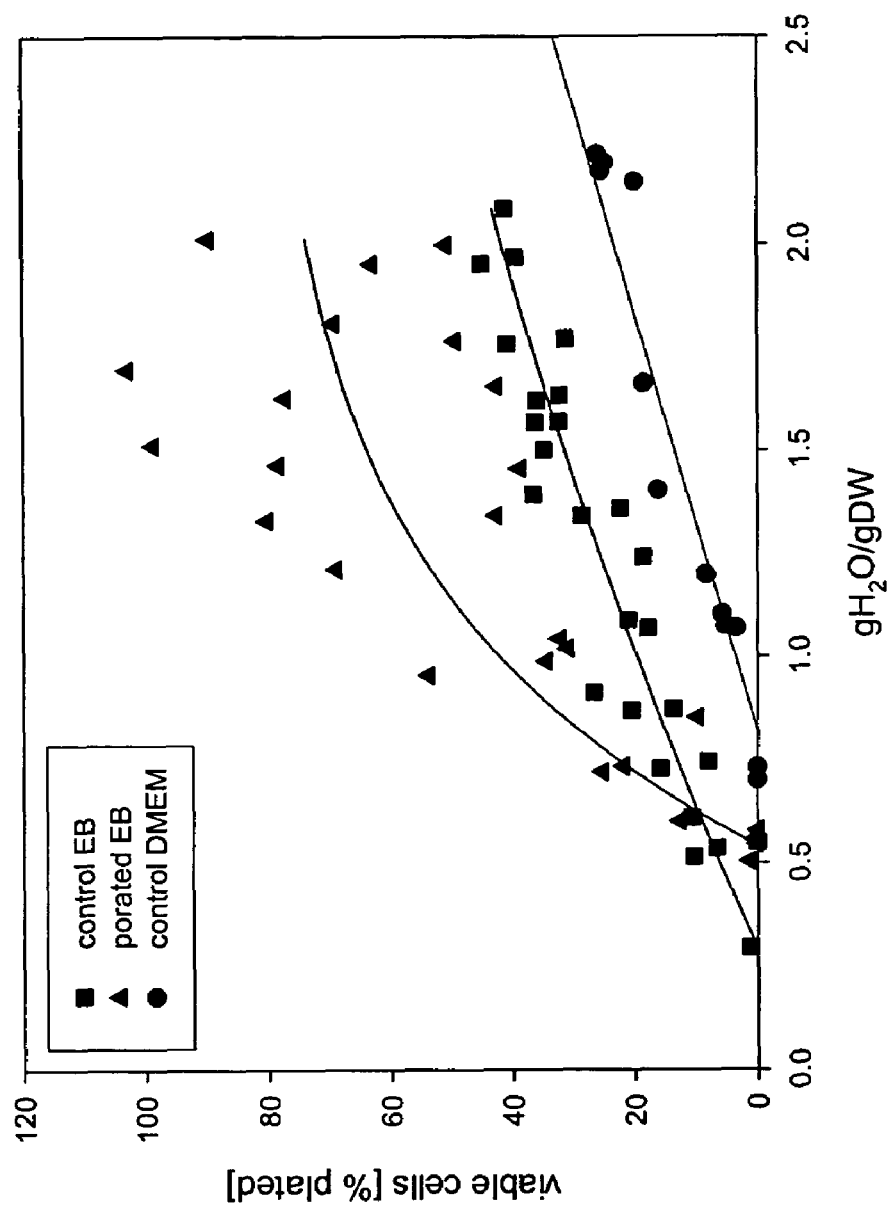
FIG. 9 depicts the percentage of plated cells with intact membranes the following day (viable cells), at different moisture levels, for different drying media, for porated and non-porated cells (control).

In this series of experiments, we assessed the effect of drying cells in an experimental drying buffer (EB) containing 250 mM trehalose, 1 mM $MgSO_4$, 5 mM glucose, 0.5 mM α-lipoic acid, 10 mM NaCl, 0.1 mM EDTA, 10 mM pyruvate and 50 mM $K_2HPO_4/KH_2PO_4$, pH 7.0, versus drying in diluted DMEM containing 200 mM trehalose. Control EB and control DMEM cells received no poration prior to drying. EB cells were porated for 10 min at 37° C. as otherwise described above, held for 90 min at 0° C., and then allowed to recover for 18 hours in DMEM cell culture medium prior to drying. After these treatments the cells were air-dried in their respective media to various moisture levels, as described above. FIG. 9 depicts the percentage of plated cells with intact membranes the following day (viable cells), at different moisture levels, for different drying media, for porated and non-porated cells (control). Each point represents the mean of 10 cell counts. (For simplicity, standard deviations are not shown. Standard deviations were in the same range as shown in FIG. 8.) As shown in FIG. 9, cells that were dried in EB had higher viability than cells dried in diluted DMEM. The combination of ATP-poration with drying in EB had a synergistic effect on post-drying viability, yielding results that were superior both to drying in EB (without ATP-poration), and to drying in DMEM (with ATP-poration).

EXAMPLE 11

Figure 10:
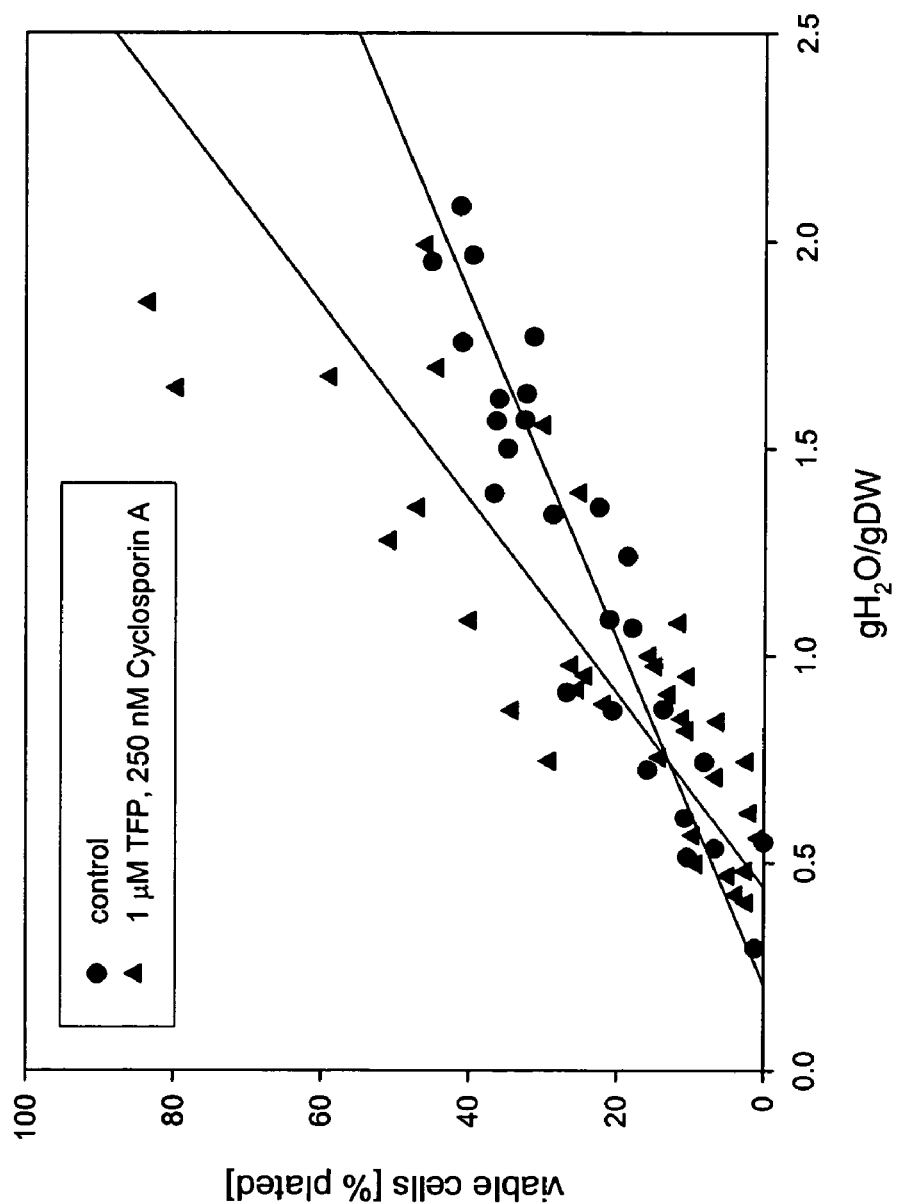
FIG. 10 depicts the percent of viable cells observed at different moisture levels for cells, for cells exposed to the apoptosis inhibitors and for control cells.

In this series of experiments, we observed the effect of two apoptosis inhibitors (cyclosporin A and Trifluoperazine; both obtained from Sigma-Aldrich, St. Louis, Mo.) on viability after air-drying. Cells were dried in an experimental drying buffer (EB) containing 250 mM trehalose, 1 mM $MgSO_4$, 5 mM glucose, 0.5 mM α-lipoic acid, 10 mM NaCl, 0.1 mM EDTA, 10 mM pyruvate, and 50 mM $K_2HPO_4/KH_2PO_4$, pH 7.0. Control cells were dried as described above. Treated cells were exposed to 1 µM Trifluoperazine (TFP) and 200 nM cyclosporin A. Cells were air-dried to different moisture levels as described above, and were subsequently re-hydrated by addition of DMEM cell culture medium. For the treated cells, both of the apoptosis inhibitors were included in both the drying buffer and in the DMEM cell culture medium that was added to the cell culture plates after the air-drying process. FIG. 10 depicts the percent of viable cells observed at different moisture levels for cells, for cells exposed to the apoptosis inhibitors and for control cells. Each point represent the mean for 10 cell counts. For simplicity, standard deviations are not shown. Standard deviations were in the same range as shown in FIG. 8. Cells that had been treated adding trifluoperazine and cyclosporin A to the drying buffer and the DMEM cell culture medium used for rehydration displayed a higher viability post-drying.

Miscellaneous

In lieu of or in addition to ATP, analogs of ATP such as 2',3'-O-(benzoyl-4-benzoyl)-ATP (also known as $B_ZATP$) may also be used in practicing this invention.

The complete disclosures of all references cited in this specification are hereby incorporated by reference. Also incorporated by reference are the complete disclosures of the following, none of which are prior art to the present application: G. Elliott et al., "Rapid loading of trehalose induced in J774 mouse macrophage cells," *Cryobiology*, vol. 47, p. 247 (2004); M. Menze et al., "Altering AMP:ATP ratio in mammalian cells to depress metabolic activity," Abstract and Poster presented at the meeting of the Society of Integrative and Comparative Biology (New Orleans, La., January 2004); S. Buchanan et al., "Permeabilization of hematopoietic progenitor cells to trehalose using P2Z purinoreceptor-associated pores for the purpose of cryopreservation," *Exp. Hematology*, vol. 32, issue 7, supp. 1, p.79, abstract 196 (2004); S. Buchanan et al., "Abstract" (AAPS Biotechnology meeting, Boston, May 2004); and M. Menze et al., "Depression of cell metabolism and proliferation by membrane permeable and impermeable modulators: Role for AMP:ATP ratio," accepted for publication, *Am. J. Phys.* (in press, 2004). In the event of an otherwise irreconcilable conflict, however, the present specification shall control.

We claim:
1. A method for preserving vertebrate cells, said method comprising the steps of:
   (a) treating the vertebrate cells with a free extracellular agent comprising adenosine 5'-triphosphate or comprising 2',3'-O-(benzoyl-4-benzoyl)-adenosine 5'-triphosphate, at a pH from about 6.0 to about 9.0; wherein the membranes of the cells comprise receptors that, in response to a sufficient concentration of the extracellular agent, cause the opening of pores in the membranes; and wherein the concentration of the extracellular agent is sufficient to cause the receptors to open pores in the membranes; whereby pores are opened in the membranes that would not be open in the absence of the extracellular agent;
   (b) exposing the cells to a preservative; wherein the preservative crosses the cell membrane substantially faster while the pores are open than the preservative would cross the cell membrane under otherwise identical conditions without the opened pores; and wherein the preservative enhances viability if the cells are subsequently dehydrated, frozen, or freeze-dried;
   (c) closing the pores by reducing the concentration of the free extracellular agent, wherein the pores are closed sufficiently soon after step (a) to maintain the viability of a substantial fraction of the cells; and
   (d) dehydrating the cells, freezing the cells, or freeze-drying the cells; wherein the viability of the cells, if subsequently reconstituted or warmed, is substantially greater than would be the viability of otherwise identical cells that had not been subjected to said steps (a) through (d) prior to being dehydrated, frozen, or freeze-dried;
   wherein:
      steps (a) and (b) may be conducted in either order, or steps (a) and (b) may be conducted simultaneously; provided that steps (a) and (b) overlap for a period of time sufficient for enough of the preservative to cross the cell membranes to enhance viability if the cells are subsequently dehydrated, frozen, or freeze-dried; and
      steps (a) and (b) substantially precede step (c); and step (c) substantially precedes step (d); and
      said vertebrate cells comprise nucleated cells or erythrocytes.
2. A method as recited in claim 1, wherein the cells are mammalian cells.
3. A method as recited in claim 2, wherein the cells are human cells.
4. A method as recited in claim 2, wherein the cells are erythrocytes.
5. A method as recited in claim 1, wherein the cells are nucleated cells.
6. A method as recited in claim 1, wherein in said pore-closing step the concentration of the free extracellular agent is reduced by diluting the extracellular agent, or by reacting the extracellular agent with a divalent cation, or by reacting the extracellular agent with a chelating agent, or by degrading the extracellular agent.
7. A method as recited in claim 1, wherein step (d) comprises dehydrating the cells.
8. A method as recited in claim 1, wherein step (d) comprises freezing the cells.
9. A method as recited in claim 1, wherein step (d) comprises freeze-drying the cells.
10. A method as recited in claim 1, wherein the receptors comprise $P2X_7$ receptors.
11. A method as recited in claim 1, wherein the cells are nucleated cells of a type whose membranes do not ordinarily comprise $P2X_7$ receptors; said method additionally comprising the step, prior to step (a), of introducing into the cells DNA encoding a $P2X_7$ receptor, and allowing the cells to express the $P2X_7$ receptor and to incorporate the $P2X_7$ receptor into the cell membranes; whereby, when step (a) is subsequently conducted, substantially more pores open in the cell membranes in response to the free extracellular agent than would have opened in otherwise identical cells with membranes lacking the $P2X_7$ receptor.
12. A method as recited in claim 1, wherein the preservative has a molecular weight less than about 900 Dalton.
13. A method as recited in claim 1, wherein the preservative comprises one or more compounds selected from the group consisting of trehalose, adenosine 5'-phosphate, adenosine 5'-phosphorothioate, sucrose, sorbitol, a disaccharide, an oligosaccharide, a metabolic activator, a metabolic inhibitor, sarcosine, octopine, taurine, proline, betaine, pinitol, ectoine, N-acetyl lysine, glycosylglycerate, and sulfotrehalose.
14. A method as recited in claim 1, wherein the preservative comprises trehalose.
15. A method as recited in claim 1, wherein the preservative comprises adenosine 5'-phosphorothioate.
16. A method as recited in claim 1, wherein step (a) is conducted at physiological temperature, and wherein step (b) is conducted at a substantially lower temperature that does not freeze the cells.
17. A method as recited in claim 1, wherein step (a) is conducted at about 37° C., and wherein step (b) is conducted at about 0° C.
18. A method as recited in claim 1, wherein the concentration of carbon dioxide during step (a) is not substantially above the ambient concentration of carbon dioxide.
19. A method as recited in claim 1, wherein step (a) is conducted at a pH from about 6.5 to about 8.0.
20. A method as recited in claim 1, wherein step (a) is conducted at a pH about 7.0.
21. A method as recited in claim 1, additionally comprising the step, after step (b), of adding an apoptosis inhibitor to the cells.
22. A method as recited in claim 21, wherein the apoptosis inhibitor comprises cyclosporin A or trifluoperazine.
23. A method as recited in claim 1, wherein the free extracellular agent comprises adenosine 5'-triphosphate.
24. A method as recited in claim 1, wherein the free extracellular agent comprises 2',3'-O-(benzoyl-4-benzoyl)-adenosine 5'-triphosphate.
25. A method as recited in claim 1, additionally comprising a step, substantially after said pore-closing step, and substantially preceding step (d): of allowing the cells to recover under non-stressful conditions, for a time that is sufficiently long to enhance viability if the cells are subsequently dehydrated, frozen, or freeze-dried; and sufficiently short to retain enough preservative within the cells to enhance viability if the cells are subsequently dehydrated, frozen, or freeze-dried.
26. A method as recited in claim 25, wherein said recovering step occurs in a nutrient medium.
27. A method as recited in claim 1, additionally comprising the step, after step (d), of reconstituting or warming the preserved cells, and restoring the normal metabolism of at least some of the cells.

* * * * *

UNITED STATES PATENT AND TRADEMARK OFFICE
CERTIFICATE OF CORRECTION

PATENT NO. : 7,314,755 B2
APPLICATION NO. : 10/965039
DATED : January 1, 2008
INVENTOR(S) : Steven C. Hand et al.

Page 1 of 1

It is certified that error appears in the above-identified patent and that said Letters Patent is hereby corrected as shown below:

Column 1, lines 9-10:

Replace "Defense Advanced Research Projects Agency" with --Naval Research Laboratory--

Signed and Sealed this

Third Day of June, 2008

JON W. DUDAS
*Director of the United States Patent and Trademark Office*